United States Patent
Khamphilavong et al.

(10) Patent No.: US 10,224,131 B2
(45) Date of Patent: Mar. 5, 2019

(54) SENSOR ASSEMBLY AND CABLE ASSEMBLY HAVING TWISTED PAIRS

(71) Applicant: TE CONNECTIVITY CORPORATION, Berwyn, PA (US)

(72) Inventors: Malai Hongthong Khamphilavong, Woodburn, OR (US); Arthur G. Buck, Sherwood, OR (US); Yevgeniy Mayevskiy, Nerberg, OR (US); Damian J. Mecham, Salem, OR (US)

(73) Assignee: CREGANNA UNLIMITED COMPANY, Galway (IE)

( * ) Notice: Subject to any disclaimer, the term of this patent is extended or adjusted under 35 U.S.C. 154(b) by 0 days.

(21) Appl. No.: 15/445,004

(22) Filed: Feb. 28, 2017

(65) Prior Publication Data

US 2018/0247740 A1    Aug. 30, 2018

(51) Int. Cl.
*H01B 11/00* (2006.01)
*H01B 11/02* (2006.01)
(Continued)

(52) U.S. Cl.
CPC ............ *H01B 11/02* (2013.01); *A61B 8/4411* (2013.01); *A61B 8/4427* (2013.01);
(Continued)

(58) Field of Classification Search
CPC ........ H01B 11/203; H01B 11/06; H01B 7/04; H01B 7/0892; H01B 11/002; H01B 11/10;
(Continued)

(56) References Cited

U.S. PATENT DOCUMENTS

| 5,491,299 A * | 2/1996 | Naylor | H01B 11/06 |
| | | | 174/113 R |
| 6,452,107 B1 * | 9/2002 | Kebabjian | H01B 11/002 |
| | | | 174/113 R |

(Continued)

FOREIGN PATENT DOCUMENTS

| CN | 202601258 U | 12/2012 |
| DE | 2523653 A1 | 12/1976 |

OTHER PUBLICATIONS

James Morizo et al.; 15 Channel Wireless Headstage System for Single Unit Rat and Primate Recordings; Research Gate Paper Identification No. No. TBME-00565-2005; Nov. 2005; 7 pages.

(Continued)

*Primary Examiner* — Angel R Estrada (57) ABSTRACT

Sensor assembly includes a modular device and a cable assembly configured to communicatively couple the modular device and a control system and transmit digital signals therethrough. The cable assembly includes a cable jacket surrounding a channel and a twisted pair extending through the channel. The coated twisted pair includes first and second signal wires that each include a respective signal conductor and an insulation layer that surrounds the respective signal conductor. The coated twisted pair also includes a ground conductor. The first and second signal wires are twisted about one another. A twist exterior is defined by corresponding exterior surfaces of the first and second signal wires and the ground conductor. The twist exterior is coated with a conductive material.

11 Claims, 5 Drawing Sheets

(51) Int. Cl.
*H01B 11/08* (2006.01)
*A61B 8/00* (2006.01)
*A61B 90/00* (2016.01)
*A61N 1/372* (2006.01)
*H01B 11/10* (2006.01)
*H01B 7/08* (2006.01)

(52) U.S. Cl.
CPC ........ *A61B 90/361* (2016.02); *A61N 1/37217* (2013.01); *H01B 11/08* (2013.01); *H01B 11/1058* (2013.01); *H01B 11/1066* (2013.01); *H01B 11/1091* (2013.01); *A61B 8/44* (2013.01); *A61B 8/56* (2013.01); *A61B 2562/221* (2013.01); *A61B 2562/222* (2013.01); *A61B 2562/227* (2013.01); *H01B 7/0892* (2013.01)

(58) Field of Classification Search
CPC ..... H01B 11/02; H01B 11/08; H01B 11/1058; H01B 11/1066; H01B 11/1091; H01R 9/00; H01R 9/03; H01R 9/032; H01R 9/034; H01R 9/05; H01R 9/0503; A61B 8/4411; A61B 8/4427; A61B 90/361; A61B 2562/222; A61B 2562/227; A61B 8/44; A61B 8/56; A61B 2562/221; A61N 1/37217
USPC ......... 174/113 R, 110 R, 68.1, 119 C, 120 C, 174/128.1, 128.2, 125.1, 36, 102 R, 174/117 R, 117 F, 126.1, 126.2
See application file for complete search history.

(56) References Cited

U.S. PATENT DOCUMENTS

| | | | | |
|---|---|---|---|---|
| 6,580,034 | B2 * | 6/2003 | Daane | H01B 7/0892 |
| | | | | 174/113 R |
| 6,734,362 | B2 * | 5/2004 | Buck | H01B 7/041 |
| | | | | 174/113 R |
| 8,378,217 | B2 * | 2/2013 | Sugiyama | H01B 11/203 |
| | | | | 174/113 R |
| 8,546,690 | B2 * | 10/2013 | Masakazu | H01B 11/002 |
| | | | | 174/113 A |
| 9,018,529 | B2 * | 4/2015 | Sidlyarevich | H01B 7/04 |
| | | | | 174/110 R |
| 9,324,478 | B2 | 4/2016 | Horan et al. | |
| 9,899,128 | B1 * | 2/2018 | Boyer | H01B 11/10 |
| 2005/0006126 | A1 | 1/2005 | Aisenbrey | |
| 2014/0209346 | A1 | 7/2014 | Buck et al. | |
| 2014/0209347 | A1 | 7/2014 | Buck et al. | |
| 2015/0075838 | A1 | 3/2015 | Buck et al. | |

OTHER PUBLICATIONS

TE Medical; Innovations in imaging and ultrasound; 2 pages.
In Vivo Calcium Imaging to Illuminate Neurocircuit Activity Dynamics Underlying Naturalistic Behavior; American College of Neuropsychopharmacology; 2015; 2 pages.
Resendez et al.;Visualization of cortical, subcortical and deep brain neural circuit dynamics during naturalistic mammalian behavior with head-mounted microscopes and chronically implanted lenses; Nature Protocols; vol. 11. No. 3; 2016; 32 pages.
International Search Report dated Jun. 14, 2018, for corresponding International Patent Application No. PCT/US2018/020026.

* cited by examiner

SENSOR ASSEMBLY AND CABLE ASSEMBLY HAVING TWISTED PAIRS

BACKGROUND

The subject matter set forth herein relates generally to cable assemblies that communicate data between a sensor and a system that processes the data.

There is a general market demand in the electrical and/or optical technology industries that use cable assemblies to reduce at least one of the size, weight, and/or cost of the cable assemblies. In some industries, such as the medical device industry, the cable assemblies are configured to transmit data between a sensor and a system that processes the data. The sensor may be handheld and/or one that is sized for insertion into a patient's body.

For example, an ultrasound system uses a cable assembly to interconnect an ultrasound device (or ultrasound probe) to a control system. High-end medical ultrasound imaging utilizes tens and hundreds of piezo-electric transducer elements to achieve a quality image that can be helpful for diagnosing a condition of the patient and/or assessing the condition of the patient. The transducer elements require individual pathways or conductors to the control system. Conventional ultrasound cable assemblies may bundle the conductors in a concentric configuration with the conductors being wrapped around one axis of the cable assembly. In order to maintain a practical size of the cable assembly and not to impose excessive stress on the sonographer, the conductors are small coaxial conductors, which may be referred to as micro-coaxial conductors. Examples of such micro-coaxial conductors include 42 AWG coaxial conductors or smaller.

Although these micro-coaxial conductors are sufficient for performing their intended functions, some challenges may still exist. For instance, it may be desirable to have cable assemblies that weigh less or are easier to move than the above cable assemblies. Tests or experiments may require positioning a video sensor on an animal or object. It is generally desirable to reduce any effect that the weight or strain of the cable assembly has on the animal or object. In addition to this, it can be difficult to fit numerous signal lines, such as 64, 128, or 256 separate micro-coaxial conductors, into a cable assembly while keeping the cable assembly small enough so that the cable assembly has a practical size and flexibility for the user. It can also be costly to produce the micro-coaxial conductors (or the cable assemblies that include such conductors) and terminate them to the sensor.

BRIEF DESCRIPTION

In an embodiment, a sensor assembly is provided that includes a modular device having a sensor configured to detect analog signals from an environment. The sensor includes a signal analog/digital converter that is configured to transform the analog signals into digital signals. The sensor assembly also includes a cable assembly configured to communicatively couple the modular device and a control system and transmit the digital signals therethrough. The cable assembly includes a cable jacket surrounding a channel and a twisted pair extending through the channel. The coated twisted pair includes first and second signal wires that each include a respective signal conductor and an insulation layer that surrounds the respective signal conductor. The coated twisted pair also includes a ground conductor. The first and second signal wires are twisted about one another. A twist exterior is defined by corresponding exterior surfaces of the first and second signal wires and the ground conductor. The twist exterior is coated with a conductive material.

In some aspects, the conductive material is less conductive than the signal conductors of the first and second signal wires or the ground conductor. For example, the conductive material may have a sheet conductivity of at least 0.2 Siemens per square mil (in which a "mil" is one thousandth of an inch) (or at least 0.00787 Siemens per square micrometer). In some aspects, the conductive material includes a binder material having conductive particles dispersed therein.

In some aspects, the ground conductor has a diameter and the signal conductors have a diameter. The diameter of the ground conductor may be greater than the diameter of the signal conductors.

In some aspects, the cable assembly is devoid of a braided shield or conductive foil that immediately surrounds the coated twisted pair. For example, the coated twisted pair may not be in direct contact with a braided shield or conductive foil or in direct contact with another layer that is directly surrounded by a braided shield or conductive foil.

In some aspects, the first and second signal wires are terminated to conductive elements of the modular device. The first and second signal wires are configured for differential signal transmission.

In some aspects, the sensor assembly includes a bundle of the coated twisted pairs. Each of the coated twisted pairs is discrete with respect to other twisted pairs of the bundle. The bundle extends through the channel of the cable assembly. An average thickness of the conductive coating may be, for example, at most 0.02 millimeters. Optionally, each of the coated twisted pairs is surrounded by a respective outer layer that is discrete with respect to the outer layers of the other twisted pairs. For example, an outer diameter of the coated twisted pair as defined by the outer layer may be 15 mils (in which a "mil" is one thousandth of an inch) (15 mils is equal to 0.381 mm). In some embodiments, the outer diameter of the coated twisted pair with jacket may be at most 45 mils (or at most 1.143 mm) or at most 43 mils (or at most 1.092 mm) without the jacket. However, it should be understood that embodiments may have outer diameters that are greater than 45 mils.

In some aspects, the modular device includes at least one of an ultrasound device, an image sensor, or an implant. In some aspects, the sensor assembly may be used for medical application. In other aspects, however, the sensor assembly may be used for purposes other than medical applications. For example, the modular device may include an imaging sensor (e.g., CMOS) or other type of sensor/transducer that detects parameters in an external environment (e.g., temperature or pressure) and communicates data to the control system.

In an embodiment, a cable assembly is provided that includes a cable jacket surrounding a channel and a bundle of twisted pairs extending through the channel. The coated twisted pairs include first and second signal wires that each include a respective signal conductor and an insulation layer that surrounds the respective signal conductor. The coated twisted pairs also include respective ground conductors. For each of the coated twisted pairs of the bundle, the first and second signal wires are twisted about one another and the ground conductor extends along the first and second signal wires. A twist exterior is defined by corresponding exterior surfaces of the first and second signal wires and the ground conductor. The twist exterior is coated with a conductive material.

In some aspects, the conductive material is less conductive than the signal conductors of the first and second signal wires or the ground conductor. The conductive material may have a sheet conductivity of at least 0.2 Siemens per square mil (or at least 0.00787 Siemens per square micrometer).

In some aspects, the cable assembly is devoid of a braided shield or a conductive foil that immediately surrounds the bundle of twisted pairs.

In some aspects, each of the coated twisted pairs is surrounded by a respective outer layer that is discrete with respect to the outer layers of the other twisted pairs.

In some aspects, each of the coated twisted pairs is devoid of a braided shield or a conductive foil that is disposed between the outer layer and the first and second signal wires and the ground conductor. Optionally, an outer diameter of the coated twisted pairs as defined by the outer layer is at most 45 mils and an average thickness of the conductive coating of the coated twisted pairs is at most 0.02 millimeters.

In an embodiment, a twisted pair is provided that includes first and second signal wires that each include a respective signal conductor and an insulation layer that surrounds the respective signal conductor. The first and second signal wires are twisted about one another. The coated twisted pair also includes a ground conductor extending along the first and second signal wires, wherein a twist exterior is defined by corresponding exterior surfaces of the first and second signal wires and the ground conductor. The coated twisted pair also includes a conductive material coated onto the twist exterior. The conductive material is less conductive than the signal conductors of the first and second signal wires or the ground conductor and has a conductivity of at least 0.2 Siemens per square mil (or at least 0.00787 Siemens per square micrometer).

In some aspects, the coated twisted pair is surrounded by a respective outer layer. Optionally. an outer diameter of the coated twisted pair as defined by the outer layer is at most 45 mils. In some aspects, an average thickness of the conductive material is at most 0.02 millimeters.

DETAILED DESCRIPTION

Embodiments set forth herein include coated twisted pairs of insulated wires and cables assemblies having the coated twisted pairs extending therethrough. Embodiments set forth herein also include systems and sensor assemblies that include cable assemblies having such twisted pairs. As used herein, a "twisted pair" includes first and second insulated signal wires that are twisted about one another or about a central axis in a helical manner. The first and second signal wires are typically twisted at a rate that is uniform throughout. Each of the first and second signal wires includes a signal conductor and an insulation layer that surrounds the signal conductor. Optionally, the coated twisted pair may include one or more ground conductors that extends alongside the first and second signal wires. The ground conductors may also be referred to as drain wires.

Embodiments also include a conductive coating that surrounds the first and second signal wires and the ground conductor. More specifically, the coated twisted pair has a twist exterior that is defined by the exterior surfaces of the first and second signal wires and the exterior surface of the optional ground conductors. The conductive material is coated onto the twist exterior. After the conductive material is cured, the conductive material surrounds the insulation of the first and second signal wires and the one or more ground conductors. The conductive material may completely surround the first and second signal wires and the ground conductor such that the conductive material forms a common outer surface of the coated twisted pair. It is contemplated that portions of the exterior surfaces of the first and second signal wires and the ground conductor may not be covered by the conductive material such that the respective surfaces are exposed.

Although various diameters may be used, embodiments may be particularly suitable for conductors of twisted pairs that are 32 American Wire Gauge (AWG) or greater. For example, embodiments may be particularly suitable for conductors of twisted pairs having diameters that are at most 0.230 mm. In particular embodiments, the conductors may be 38 AWG or greater or have an outer diameter that is at most 0.120 mm. In more particular embodiments, the conductors may be 40 AWG or greater or have an outer diameter that is at most 0.080 mm. In more particular embodiments, the conductors may be 42 AWG or greater or have an outer diameter that is at most 0.065 mm.

Embodiments set forth herein may have an improved performance compared to conventional cable assemblies that include coaxial conductors and/or a reduced cost compared to conventional cable assemblies that include coaxial conductors. Moreover, the coated twisted pairs set forth herein may have an improved performance compared to twisted pairs that do not include the conductive material or coating. For example, at least one technical effect of one or more embodiments may include reduced jitter. Another technical effect of one or more embodiments may include a reduction in the outer diameter (or maximum diameter) of the insulated wires or in the coated twisted pair. Another technical effect of one or more embodiments may include an increase in flexibility of the cable assembly compared to conventional cable assemblies that include coaxial conductors. The cable assemblies may weigh less than the conventional cable assemblies. Another technical effect of one or more embodiments may include a reduced number of components and/or steps performed when constructing the cable assembly compared to conventional cable assemblies that include coaxial conductors. It should be understood that each and every embodiment set forth herein may not have each and every technical effect provided above.

Figure 1:
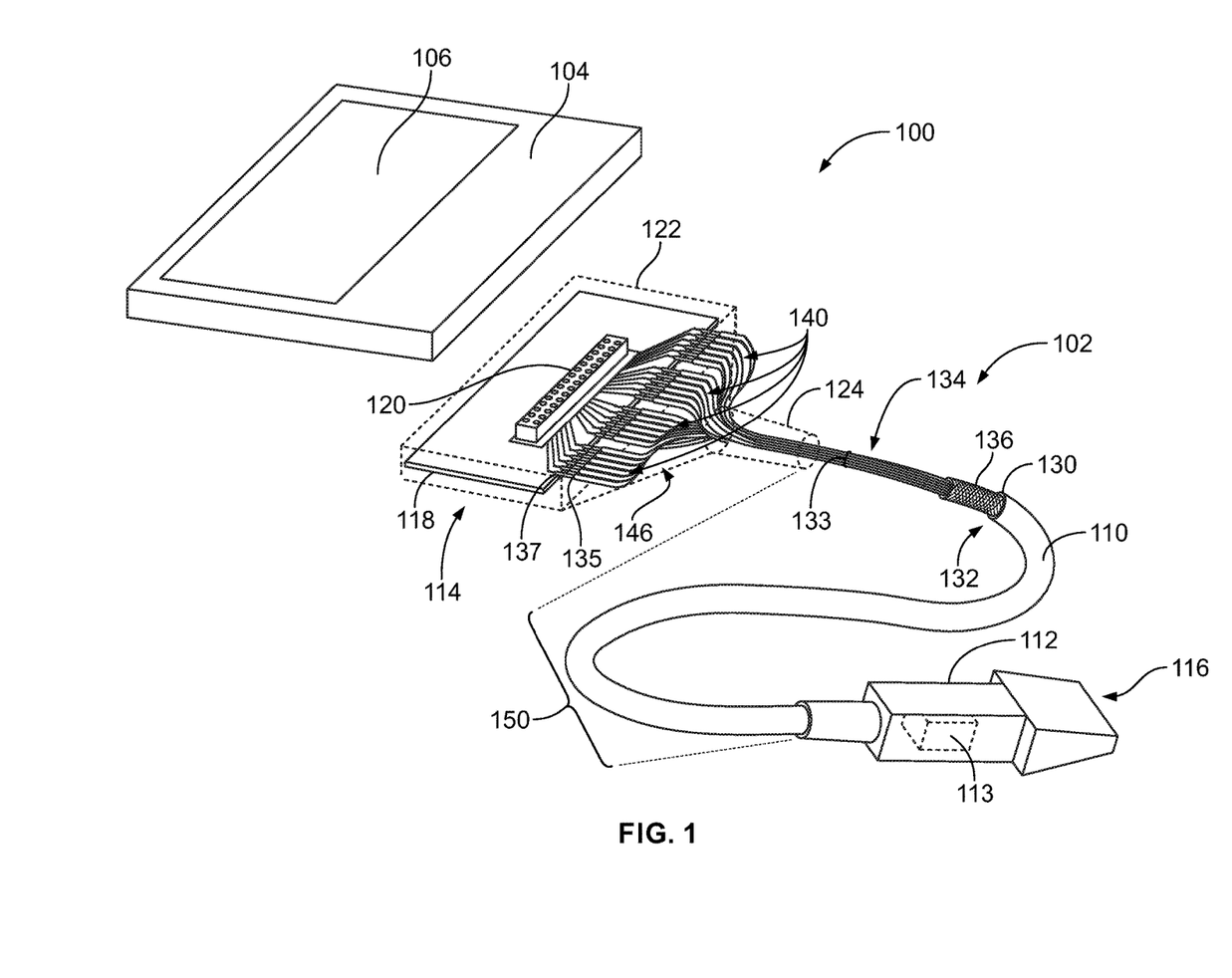
FIG. 1 is a perspective view of a system that includes a control system and a sensor assembly formed in accordance with an embodiment and a cable assembly.

FIG. 1 illustrates a system 100 formed in accordance with an embodiment that includes a sensor assembly 102 and a control system 104 that are communicatively coupled to one another. The sensor assembly 102 includes a cable assembly 110 and a sensor 112. The sensor 112 may include a plurality of components (e.g., electrodes, circuit board, signal converter, etc.) that are configured to process signals. The signals are a function of the external environment of the sensor 112. Because the sensor 112 may be part of a larger standalone device, the sensor 112 is hereinafter referred to as a modular device 112. The sensor 112 includes a signal analog/digital converter 113 that is configured to transform the analog signals generated by the sensor 112 into digital signals that are communicated through the cable assembly 110.

In the illustrated embodiment, the modular device 112 is an ultrasound device, but it is contemplated that other devices may be used. For example, the modular device 112 may be an image sensor, a pressure sensor, a temperature sensor, a cardiac pacemaker, a neurostimulator, or an implant. The cable assembly 110 extends between and communicatively couples the modular device 112 and the control system 104.

Although the cable assembly 110 is illustrated as communicatively coupling the modular device 112 and the control system 104, it should be understood that the cable assembly 110 may be used for a variety of applications. In particular, the cable assembly 110 may include twisted pairs of different twists and/or twisted pairs having different braided arrangements in which the insulated wires electrically couple different components. For example, the modular device 112 may include an imaging sensor (e.g., CMOS) or other type of sensor/transducer that detects external signals and communicates the external signals, directly or indirectly, to a control system 104. Accordingly, unless explicitly recited otherwise in the claims, the cable assemblies set forth herein are not limited to sensor assemblies.

In the illustrated embodiment, the control system 104 is a portable user device having a display 106. For example, the control system 104 may be a tablet computer. In other embodiments, the control system 104 may be a laptop computer or smartphone. Yet in other embodiments, the control system 104 may be a larger control system, such as a workstation. The control system 104 may include one or more processors (or processing units) that are configured to execute programmed instructions. For example, the control system 104 may receive data signals (e.g., digital signals) that are based on external signals detected by the sensor assembly 102, process the data signals, and generate useful information for the user.

The control system 104 may transform the data signals into images that are shown on the display 106. The display 106 may include a touch screen that is configured to receive user inputs such that a user may control operation of the system 100 through the touch screen. Alternatively or in addition to the touchscreen, the control system 104 may include an input device, such as a keyboard or touchpad, for receiving user inputs. The control system 104 may also be configured to communicatively couple to an external input device, such as a mouse or external keyboard. In some embodiments, the control system 104 may transmit signals to emit energy from a modular device 112 of the sensor assembly 102.

In an exemplary embodiment, the sensor assembly 102 is used for ultrasound imaging. In some embodiments, the modular device 112 may be used as a catheter that is configured to be inserted into a body (e.g., human or animal). For example, the sensor assembly 102 may be configured for real-time three-dimensional (3D) ultrasound imaging. Ultrasound can be excited by many different methods, including the piezoelectric effect, magnetostriction, and the photoacoustic effect.

As shown in FIG. 1, the modular device 112 is an ultrasound probe. In some embodiments, the modular device 112 may be or include a piezoelectric micromachined ultrasonic transducer (PMUT) or a capacitive micromachined ultrasonic transducer (CMUT). The modular device 112 may be or include a solid state device, such as complementary metal-oxide semiconductors (CMOSs), charge-coupled devices (CCDs), and the like. The modular device 112 may be sized for insertion into, for example, a patient's body. In some embodiments, the modular device 112 is configured to detect or observe external signals.

In other embodiments, the modular device 112 may include or constitute an imaging sensor (e.g., CMOS). The modular device 112 may also be configured to measure conditions within a designated space, such as pressure or temperature. The modular device 112 may also be configured for stimulation by delivering electrical pulses. It should be understood that the modular device 112 may also be configured for both detection and therapy in some embodiments.

The sensor assembly 102 has a connector end 114, a device end 116, and the cable assembly 110 extending therebetween. The cable assembly 110 has a cable jacket 130 that defines a channel 132 that extends lengthwise along the cable jacket 130. The cable assembly 110 also includes a plurality of twisted pair cables 134 that extend through the channel 132. The twisted pair cables 134 may be similar or identical to the twisted pair cables 160 (shown in FIG. 3). When collected in a group or bunch, the twisted pair cables 134 may be referred to as a bundle 133 of twisted pair cables. In the illustrated embodiment, the cable assembly 110 also includes a shield layer 136 (e.g., braided shield) that surrounds the plurality of twisted pair cables 134. In other embodiments, however, the cable assembly 110 is devoid of a shield layer or, more specifically, of a braided shield or a conductive foil that immediately surrounds the bundle of twisted pair cables 134. In particular embodiments, the twisted pair cables 134 are devoid of individual shield layers, such as braided shields or conductive foils, that immediately surround the wires of the corresponding twisted pairs.

The connector end 114 and device end 116 are shown as examples of components that can be interconnected by the cable assembly 110. In the illustrated embodiment, the connector end 114 includes a printed circuit 118 having a system connector 120 mounted thereto for connection to the control system 104. The printed circuit 118 may be, for example, a printed circuit board (PCB) or a flex circuit. In alternative embodiments, the twisted pair cables 134 may be terminated directly to the control system 104. The connector end 114 also includes a housing 122 and strain relief 124.

Figure 2:
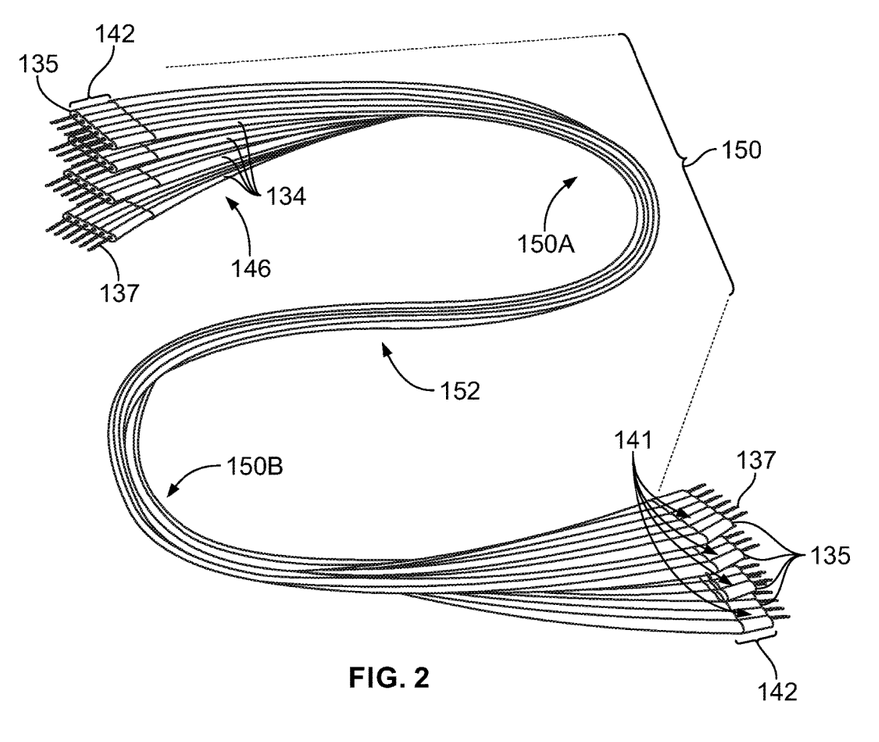
FIG. 2 is a perspective view of the cable assembly of FIG. 1 formed in accordance with an embodiment.

As shown in FIGS. 1 and 2, the twisted pair cables 134 are arranged into designated groups 140 proximate to the connector end 114 and designated groups 141 (FIG. 2) proximate to the device end 116. Each of the designated groups 140, 141 includes a plurality of the twisted pair cables 134. More than one group 140 may be stacked or positioned adjacent to one another at the connector end 114. Likewise, more than one group 141 may be stacked or positioned adjacent to one another at the device end 116.

The twisted pair cables 134 of a designated group 140 (or 141) are coupled to one another proximate to wire ends 135 of the twisted pair cables 134 such that the twisted pair cables 134 have substantially fixed positions with respect to one another proximate to the wire ends 135. The wire ends 135 include an end of insulation of the insulated wire. By way of example, the twisted pair cables 134 may be coupled in substantially fixed positions with respect to one another by tape 142 (FIG. 2). Alternatively, the insulation of the twisted pair cables 134 of one designated group 140 may be combined such that a single section of insulation holds the conductors of the twisted pair cables 134 in substantially fixed positions with respect to one another proximate to the wire ends 135. The single section of insulation may correspond to the same section provided by the tape 142. The twisted pair cables 134 may separate from one another as the twisted pair cables 134 extend toward the other end.

It should be understood that when the twisted pair cables 134 are held in "substantially fixed positions with respect to one another proximate to the wire ends," the exposed conductors 137 of the insulated wires may still be manipulated (e.g., bent or moved) for terminating to a corresponding element. It should also be understood that other mechanisms exist for holding the twisted pair cables 134 in substantially fixed positions with respect to one another. For example, a clamp (not shown) made hold the designated group 140 (or 141) of twisted pair cables 134 or the designated group 140 (or 141) may be sandwiched between two housing shells (not shown). In some embodiments, the twisted pair cables 134 are not held in substantially fixed positions with respect to one another at the wire ends 135.

The twisted pair cables 134 of each of the designated groups 140 may correspond to a single designated group 140 at the other end of the cable assembly 110. In other words, each designated group 140 corresponds to one designated group 141 and only one designated group 141. In such embodiments, the twisted pair cables 134 may form a ribbon layer 146. FIGS. 1 and 2 show the cable assembly 110 as including four (4) ribbon layers 146. Each ribbon layer 146 has a plurality of twisted pair cables 134 that extend between the connector end 114 and the device end 116. The twisted pair cables 134 form a designated group 140 at the connector end 114 and a designated group 141 at the device end 116.

Alternatively, the twisted pair cables 134 of at least one designated group at one end of the cable assembly 110 may correspond to multiple designated groups at the other end. For example, two twisted pair cables 134 from a designated group 140 at the connector end 114 may become part of a first designated group 141 at the device end 116. Two other twisted pair cables 134 from the same designated group 140 may become part of a second designated group 141 at the device end 116 of the cable assembly 110.

The twisted pair cables 134 are typically held in substantially fixed positions at the connector end 114 and at the device end 116. An intermediate portion 150 of the cable assembly 110 may extend between the connector end 114 and the device end 116. The intermediate portion 150 includes portions of the twisted pair cables 134, which may be permitted to move with respect to one another. As shown in FIG. 2, the intermediate portion 150 of the cable assembly 110 is not constrained by tape or combined insulation as described above. The twisted pair cables 134 are only constrained at the connector end 114 and at the device end 116. As such, in some embodiments, the twisted pair cables 134 are permitted to move freely with respect to one another along the intermediate portion 150. In other embodiments, the intermediate portion 150 are tightly bunched by the cable jacket 130.

In alternative embodiments, the twisted pair cables 134 may also be constrained at other locations along the cable assembly 110. For example, the twisted pair cables 134 may be coupled together by tape at a designated point 152 along a length of the cable assembly 110. In FIG. 2, the designated point 152 is a midpoint, but other locations may be used. In such embodiments, the cable assembly 110 includes two sub-portions 150A, 150B. The sub-portion 150A extends between the connector end 114 and the midpoint 152. The sub-portion 150B extends between the device end 116 and the midpoint 152.

In some embodiments, each of the ribbon layers 146 includes a single layer of twisted pair cables 134. More specifically, the twisted pair cables 134 of the designated groups 140, 141 of each ribbon layer 146 may be coplanar with respect to one another. It is understood that the twisted pair cables 134 of one ribbon layer 146 may move with respect to one another along the loose portion 150. In other embodiments, however, the ribbon layer 146 may include multiple layers of twisted pair cables 134. For example, a designated group may include multiple rows of twisted pair cables 134 stacked with respect to one another. In some embodiments, the cable assembly 110 includes multiple ribbon layers 146. In other embodiments, however, the cable assembly 110 may include only a single ribbon layer 146. To facilitate assembly, the designated groups 140, 141 may be labeled (e.g., A, B, or C).

Figure 3:
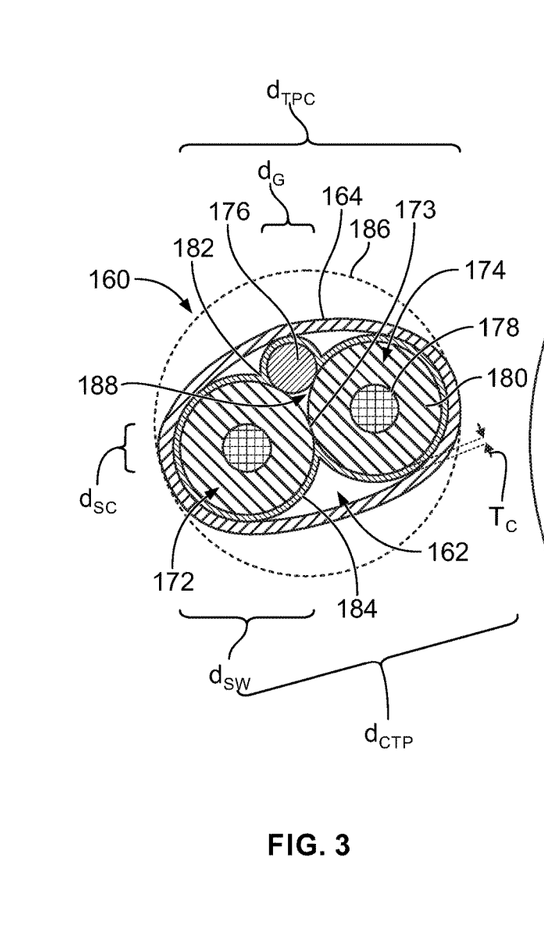
FIG. 3 illustrates a cross-section of twisted pair cable having a twisted pair of insulated wires formed in accordance with an embodiment.

FIG. 3 illustrates a cross-section of a twisted pair cable 160 in accordance with an embodiment. In FIG. 3, the twisted pair cable 160 includes a single coated twisted pair 162 and an outer layer 164 that surrounds the single coated twisted pair 162. The outer layer 164 may be, for example, an insulative layer that mechanically holds the coated twisted pair 162 so that the signal and ground conductors have essentially fixed positions with respect to one another. The outer layer 164 may be manufactured from a one or more materials, including polyvinyl chloride (PVC), polyethylene terephthalate (PET), polyvinyl fluoride, polyethylene, or paper-fiberglass laminates. In particular embodiments, the outer layer 164 is a tape that is wrapped about the coated twisted pair 162 in which each wrap of the outer layer 164 overlaps the prior wrap. Optionally, the tape may include a conductive foil.

In alternative embodiments, the outer layer 164 may be formed by a subsequent coating process after the conductive material 184 is applied. In such embodiments, the coating may include an inner layer that is conductive and extends along the insulated wires and ground conductor and an outer layer that may be insulative and extends along the inner layer.

The coated twisted pair 162 includes a first signal wire 172, a second signal wire 174, and a ground conductor 176. Each of the first signal wire 172 and the second signal wire 174 includes a signal conductor 178 and an insulation layer 180 that surrounds the signal conductor 178. The ground conductor 176 is bare such that the ground conductor 176 is not disposed within insulation.

In the illustrated embodiment, the ground conductor 176 has a diameter $d_G$ that is larger than a diameter $d_{SC}$ of the signal conductors 178 of the first and second signal wires 172, 174. In other embodiments, however, the diameter $d_G$ of the ground conductor 176 may be smaller than the diameter $d_{SC}$ of the signal conductors 178 or may be equal to the diameter $d_{SC}$ of the signal conductors 178. Also, in the illustrated embodiment, only a single ground conductor 176 is used. In other embodiments, a plurality of ground conductors 176 may be used (e.g., two or more ground conductors).

The first signal wire 172 and the second signal wire 174 are twisted about a central axis 173 of the twisted pair 162.

The ground conductor 176 extends along the twisted first and second signal wires 172, 174. Other optional ground conductors (not shown) may also be positioned extend along the twisted first and second signal wires 172, 174. The first signal wire 172, the second signal wire 174, and the ground conductor(s) 176 form a twist exterior 182. The twist exterior 182 is a composite surface that is collectively formed by the exposed exterior surfaces of the first signal wire 172, the second signal wire 174, and the ground conductor(s) 176 after the coated twisted pair 162 is operably formed. The twist exterior 182 represents an outer surface of the twisted conductors that may be coated.

During the coating process, the conductive material 184 is provided onto the twist exterior 182 by, for example, spraying, depositing (e.g., ink-printing), dipping, or otherwise having conductive material flow along the twist exterior 182. The conductive material 184 may then be baked or otherwise permitted to cure. After the conductive material 184 has cured, the conductive material may be referred to as a conductive coating 184. The conductive coating 184 is electrically coupled to the ground conductor 176, which is devoid of an insulative layer. In some embodiments, a gap or void 188 will be defined by the exterior surfaces of the first signal wire 172, the second signal wire 174, and the ground conductor 176.

The twisted pair cable 160 has a cross-sectional profile 186 (indicated by the dashed or phantom circle). The cross-sectional profile 186 is defined by an outer diameter $d_{TPC}$ (or greatest cross-sectional dimension that extends through the central axis 173) of the twisted pair cable 160. The cross-sectional profile 186 represents the space occupied by twisted pair cable 160 and accounts for the twisting of the first and second signal wires. In FIG. 3, the outer diameter $d_{TPC}$ is defined by opposite surfaces of the outer layer 164. In some embodiments, the outer diameter $d_{TPC}$ is defined by opposite surfaces of the conductive material or coating 184.

Each of the first and second signal wires 172, 174 has an outer diameter $d_{SW}$ and the conductive material or coating 184 has a thickness $T_C$. The diameters described above may also correspond to standard gauges. The various dimensions of the twisted pair cable 160, such as the outer diameter $d_{TPC}$ of the twisted pair cable 160, the diameter $d_{SC}$ of the wire conductor 178, the outer diameter $d_{SW}$ of the insulated signal wires 172, 174, the diameter $d_G$ of the ground conductor 176, and the thickness $T_C$ of the conductive coating 184, may be selected so that the design of the twisted pair cable 160 achieves a target performance. The conductor material and gauge may be selected to facilitate a desired current flow through a given conductor. For example, the gauge of the signal conductor 178 may be decreased (i.e., increased in diameter) to facilitate increased current flow. Stranded as opposed to solid conductors may be utilized to improve overall flexibility of the cable assembly.

As shown, the twisted pair cable 160 does not include a discrete shielding layer, such as a braided shield or conductive foil. This may also be characterized as the twisted pair cable 160 being devoid of a discrete shielding layer. In alternative embodiments, however, the twisted pair cable 160 may include an additional shield and/or a conductive foil.

The ground conductor 176 may be more conductive than the conductive material 184. In some embodiments, the conductive material 184 comprises an electrically-lossy material. The electrically-lossy material may be formed using a dielectric material with conductive particles (or fillers) dispersed within the dielectric material. The dielectric material, such as a polymer or epoxy, is used as a binder to hold the conductive particle filler elements in place. Although the conductive particles are conductive, the conductive particles may impart loss to the conductive material 184. Electrically-lossy material may be only partially conductive compared to the ground conductor 176. For example, the conductive material 184 may have a bulk conductivity of between 0.2 Siemens per square mil and 1.0 Siemens per square mil. The ground conductor 176 may have, for example, a bulk conductivity of between 0.277343 Siemens per meter and 0.448235 Siemens per meter. As such, the ground conductor 176 may be electrically coupled to the conductive material 184 but more conductive than the conductive material 184.

As one example, the conductive material 184 prior to the coating process may comprise carbon, graphite, graphene, silver, or copper, and may be in a suspended solution. For example, Dag 502 (also known as Electrodag 502), carbon/graphite particles in a fluoropolymer binder suspended in methylethylketone, may be used. It may be applied via a spraying or dispersion process or other process suited for applying a thin layer of conductive material. After the conductive material has cured, the outer layer 184 may be applied. When it is necessary to terminate the twisted pair cables 160, end of the twisted pair cables 160 may be stripped to expose the signal conductors and ground conductor.

Examples of conductive particles that may be used as a filler to form electrically-lossy materials include carbon or graphite formed as fibers, flakes, or other particles. Metal in the form of powder, flakes, fibers, or other conductive particles may also be used to provide suitable electrically-lossy properties. Alternatively, combinations of fillers may be used. For example, metal plated (or coated) particles may be used. Silver and nickel may also be used to plate particles. Plated (or coated) particles may be used alone or in combination with other fillers, such as carbon flake. In some embodiments, the fillers will be present in a sufficient volume percentage to allow conducting paths to be created from particle to particle. For example, when metal fiber is used, the fiber may be present in up to 40% by volume or more.

As used herein, the term "binder" encompasses a material that encapsulates the filler or is impregnated with the filler. The binder material may be any material that will set, cure, or can otherwise be used to position the filler material. In some embodiments, the binder may be a thermoplastic material such as those traditionally used in the manufacture of insulated wires or cables. However, many alternative forms of binder materials may be used. Curable materials, such as epoxies, can serve as a binder. Alternatively, materials such as thermosetting resins or adhesives may be used.

The insulation layer 180 that surrounds the signal conductor 178 may be made of a material such as a fluoropolymer, polyvinyl chloride (PVC), or polyethylene. The thickness of the insulation layer 180 may be, for example, 0.05 to 0.64 mm (0.002 to 0.015 inch). Increased thickness of the insulation layer 180 may improve the cross-talk characteristic (i.e. decreases the mutual capacitance between wires) and, therefore, lowers the cross-talk between adjacent twisted pair cables 160. On the other hand, an increase in thickness lowers a total number of twisted pair cables 160 that may be positioned within the cable assembly. The thickness of the twisted pair cables 160 may be used to control capacitance and characteristic impedance of the cable assembly.

Figure 4:
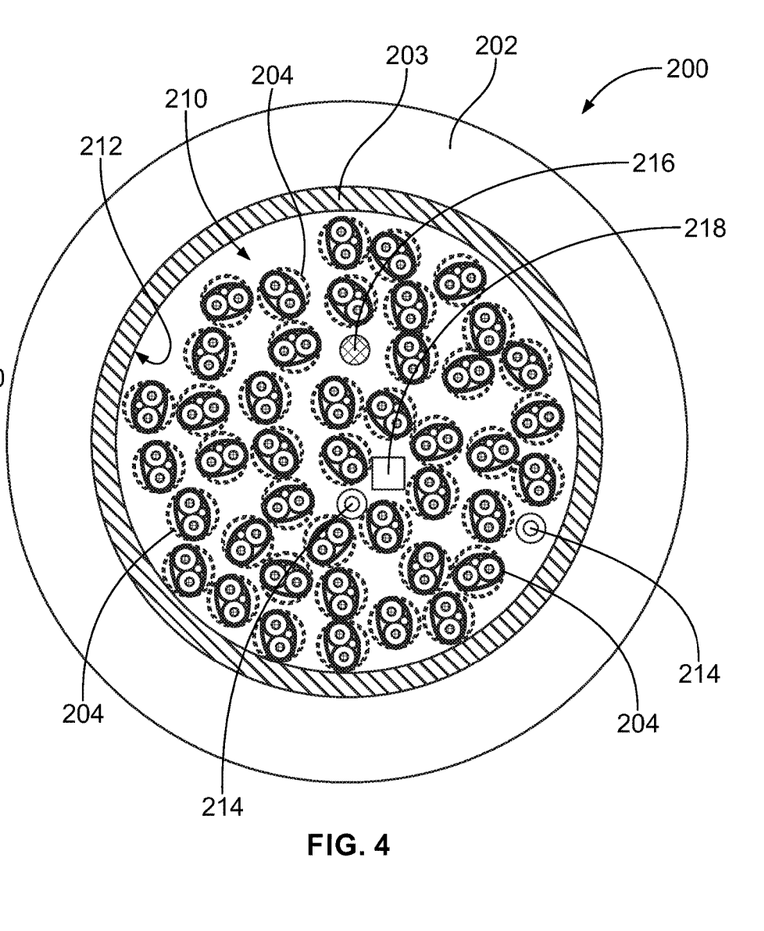
FIG. 4 is a cross-section of a cable assembly that includes the twisted pair cables of FIG. 3.

FIG. 4 is a cross-section of a cable assembly 200 in accordance with an embodiment. The cable assembly 200 may be similar or identical to the cable assembly 110 (FIG. 1). The cable assembly 200 may be configured to communicatively couple a sensor (e.g., modular device) and a control system (not shown in FIG. 4), although it is contemplated that the cable assembly 200 may be used for other applications. The cable assembly 200 includes a cable jacket 202, a discrete cable shield 203, and a plurality of twisted pair cables 204. The cable jacket 202 may comprise, for example, an insulative material. It is noted that the cable shield 203 is optional and other embodiments may be devoid of a discrete cable shield. In some embodiments, cable shield 203 may comprise braided strands of metal (e.g., copper). In other embodiments, the cable shield 203 may comprise a tape having a metallic layer (e.g., backing) that is wrapped about the twisted pair cables 204.

The cable jacket 202 surrounds a channel 210 of the cable assembly 200. However, the cable jacket 202 does not necessarily define the channel 210. As shown, an inner surface 212 of the cable shield 203 essentially defines the dimensions of the channel 210. Although the channel 210 appears to have a circular profile in FIG. 4, the channel 210 may change shape when the cable assembly 200 is squeezed and/or bent. The channel 210 may be sized to hold a designated number of twisted pair cables 204. For example, the number of twisted pair cables may be at least eight (8), at least sixteen (16), at least 32, at least 64, at least 128, at least 256, at least 512, or more. However, it should be understood that, in some embodiments, less than 8 twisted pairs may be used and, in particular embodiments, only a single twisted pair may be used.

In some embodiments, the dimensions of the channel 210 and the dimensions of the cross-sectional profiles of the twisted pair cables 204, such as the cross-sectional profiles 186 shown in FIG. 3, may be designed so that the twisted pair cables 204 within the channel 210 have a designated pack ratio. The designated pack ratio is defined as $Area^{WPS}/Area^C$ in which the $Area^{WPS}$ includes a collective cross-sectional area of the twisted pair cables and the $Area^C$ is equal to a cross-sectional area of the channel. The collective cross-sectional area of the twisted pair cables 204 may include a sum of the cross-sectional areas of the twisted pair cables 204. The cross-sectional areas of the twisted pair cables may be determined by, for example, the diameters of the twisted pair cables. The $Area^{WPS}$ represents the collective cross-sectional area of elements within the channel 210. In some embodiments, the elements within the channel 210 are only the twisted pair cables 204.

In other embodiments, however, the cable assembly 200 includes additional longitudinal elements. By way of example, the other longitudinal elements (or elongated elements that extend lengthwise through the channel 210) may include at least one of optical fibers 216, non-conductive spacers 218, or other electrical conductors 214. The other electrical conductors 214 may provide, for example, electrical power to the modular device (not shown) or may communicate data signals that differ from those communicated by the twisted pair cables 204. The optical fibers 216 may communicate data signals between different elements, and the spacers 218 may separate the longitudinal elements within the channel 210.

In some embodiments, the other longitudinal elements 214, 216, and 218 are configured to extend through and separate the twisted pair cables 204. The other longitudinal elements 214, 216, and 218 may be distributed within the channel 210 for this purpose. Yet in other embodiments, the other longitudinal elements 214, 216, and 218 may be grouped together to occupy a single cable-shaped region (not shown) within the channel 210. In such embodiments, the available space within the channel 210 for the twisted pair cables 204 to move within is reduced.

The designated pack ratio corresponds to a density of the twisted pair cables 204 within the channel 210 and may determine a level of constraint for the twisted pair cables 204 within the channel 210. By way of example, the designated pack ratio may be at most 0.95. In some embodiments, the designated pack ratio may be at most 0.80 or at most 0.70.

Figure 5:
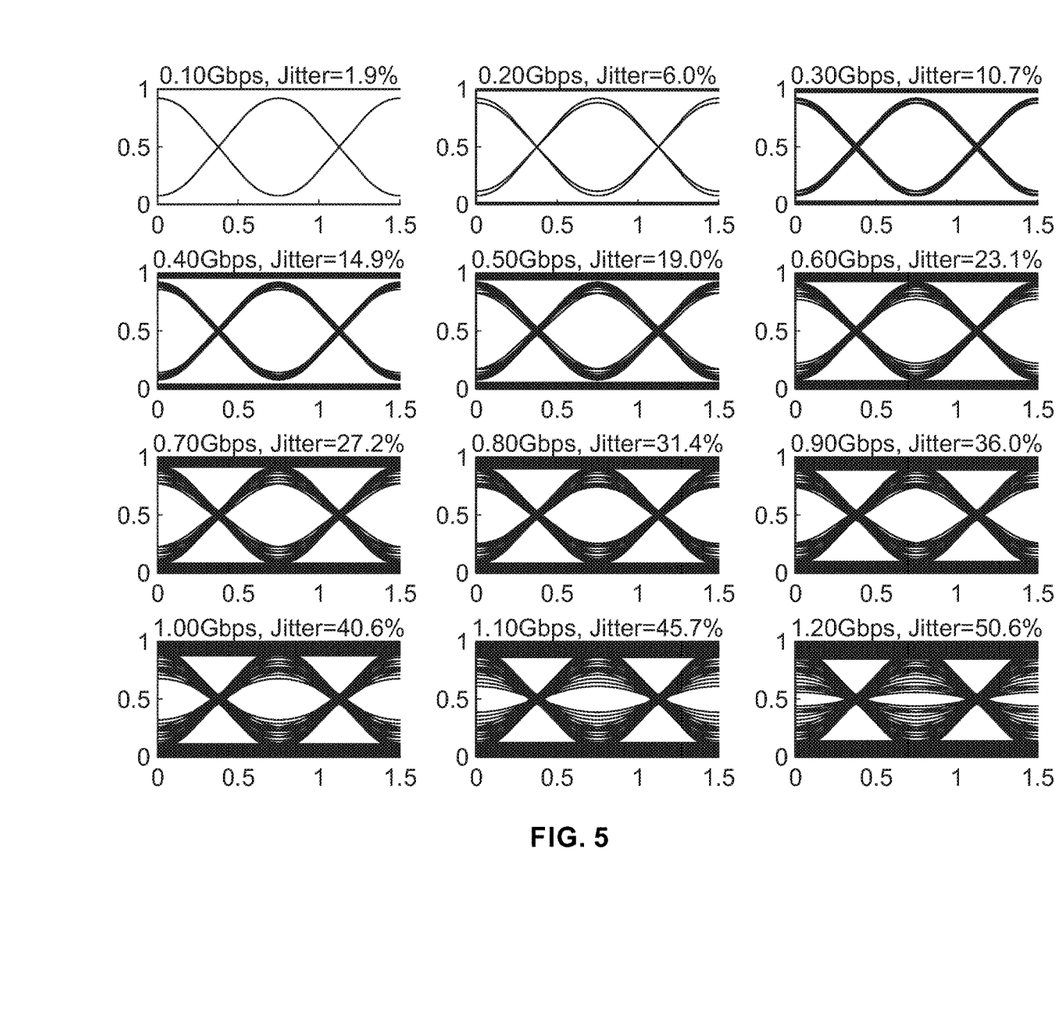
FIG. 5 illustrates a series of eye diagrams for a conventional twisted pair that illustrate a percentage of jitter as the data rates increase.
Figure 6:
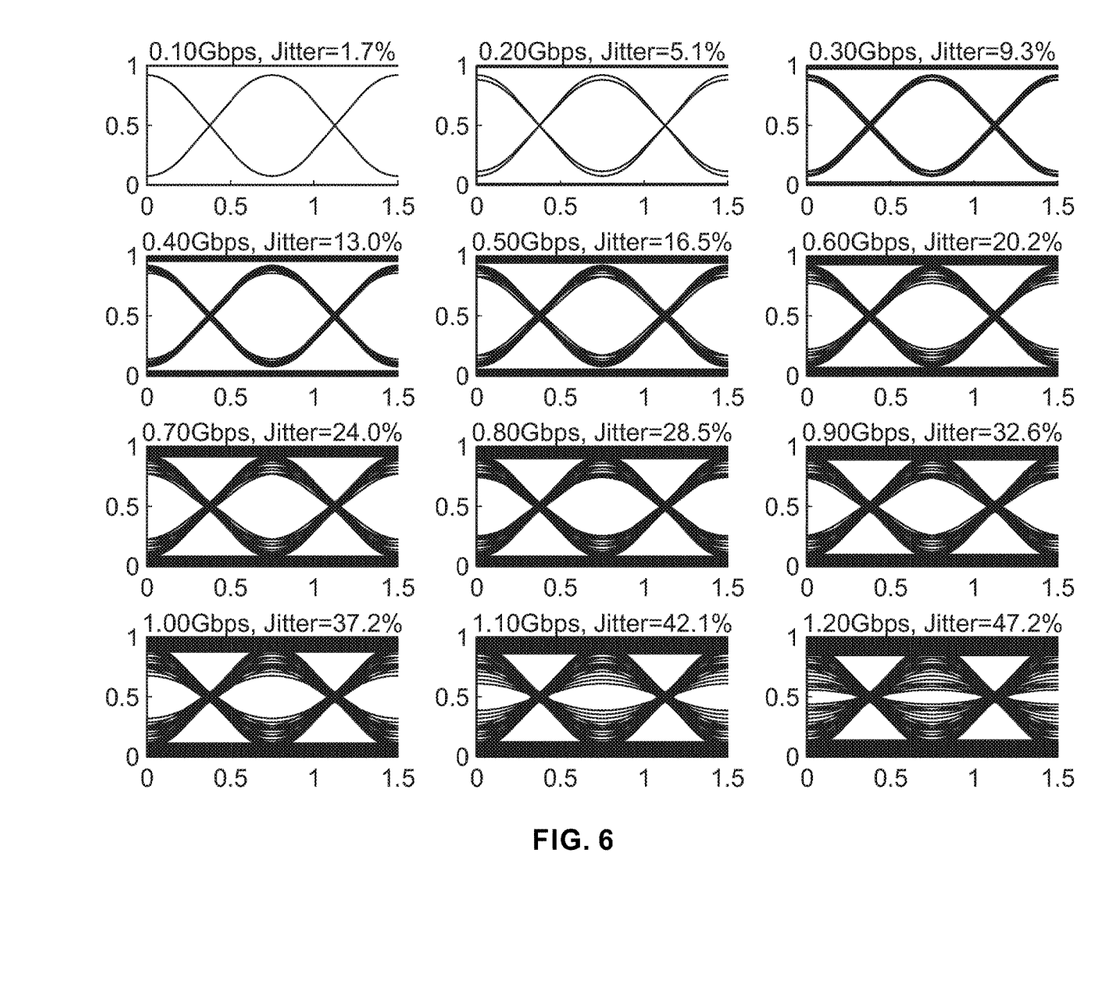
FIG. 6 illustrates a series of eye diagrams for a twisted pair having a conductive material on the twist exterior in which the eye diagrams illustrate a percentage of jitter as the data rates increase.

FIG. 5 illustrates a series of eye diagrams for a conventional twisted pair that illustrate a percentage of jitter as the data rates increase. The conventional twisted pair used during these measurements included 42 AWG signal wires comprising stranded copper and a braid shield comprising 48 AWG strands. FIG. 6 illustrates a series of eye diagrams for a twisted pair having a conductive material on the twist exterior in which the eye diagrams illustrate a percentage of jitter as the data rates increase. The twisted pair in FIG. 6 comprised 42 AWG solid copper and a 38 AWG drain wire. The eye diagrams in FIGS. 5 and 6 are based on simulations of a pseudorandom binary sequence (PRBS) 2^7 data pattern. As shown by comparing the eye diagrams, the twisted pair in FIG. 6 may have less jitter compared to the conventional twisted pair of FIG. 5 and at greater data rates.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase "in an exemplary embodiment" and the like means that the described embodiment is just one example. The phrase is not intended to limit the inventive subject matter to that embodiment. Other embodiments of the inventive subject matter may not include the recited feature or structure. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:
1. A sensor assembly comprising:
a modular device including a sensor configured to detect analog signals from an external environment, the sensor including a signal analog/digital converter that is configured to transform the analog signals into digital signals; and a cable assembly configured to communicatively couple the modular device and a control system and transmit the digital signals therethrough, the cable assembly comprising:
a cable jacket surrounding a channel; and
a coated twisted pair extending through the channel, the coated twisted pair including first and second signal wires that each include a respective signal conductor and an insulation layer that surrounds the respective signal conductor, the coated twisted pair also including a ground conductor, wherein the first and second signal wires are twisted about one another and wherein a twist exterior is defined by corresponding exterior surfaces of the first and second signal wires and the ground conductor, the twist exterior being coated with a conductive material.

2. The sensor assembly of claim 1, wherein the conductive material is less conductive than the signal conductors of the first and second signal wires or the ground conductor.

3. The sensor assembly of claim 1, wherein the conductive material has a conductivity of at least 0.2 Siemens per square mil.

4. The sensor assembly of claim 1, wherein the ground conductor has a diameter and the signal conductors have a diameter, the diameter of the ground conductor being greater than the diameter of the signal conductors.

5. The sensor assembly of claim 1, wherein the cable assembly is devoid of a braided shield or conductive foil that immediately surrounds the coated twisted pair.

6. The sensor assembly of claim 1, wherein the first and second signal wires are terminated to conductive elements of the modular device, the first and second signal wires configured for differential signal transmission.

7. The sensor assembly of claim 1, wherein the sensor assembly includes a bundle of the coated twisted pairs, each of the coated twisted pairs being discrete with respect to other twisted pairs of the bundle, the bundle extending through the channel of the cable assembly.

8. The sensor assembly of claim 7, wherein each of the coated twisted pairs is surrounded by a respective outer layer that is discrete with respect to the outer layers of the other twisted pairs.

9. The sensor assembly of claim 8, wherein an outer diameter of the coated twisted pair as defined by the outer layer is at most 15 mils.

10. The sensor assembly of claim 7, wherein an average thickness of the conductive coating is at most 0.02 millimeters.

11. The sensor assembly of claim 1, wherein the modular device includes at least one of an ultrasound device, an image sensor, or an implant.

* * * * *